US008622889B1

(12) United States Patent (10) Patent No.: US 8,622,889 B1
Loria (45) Date of Patent: Jan. 7, 2014

(54) PENILE ENHANCER APPARATUS

(76) Inventor: Victor Loria, Doral, FL (US)

(*) Notice: Subject to any disclaimer, the term of this patent is extended or adjusted under 35 U.S.C. 154(b) by 610 days.

(21) Appl. No.: 12/909,545

(22) Filed: Oct. 21, 2010

(51) Int. Cl.
*A61F 5/00* (2006.01)
(52) U.S. Cl.
USPC .......................................................... 600/38
(58) Field of Classification Search
USPC .................................................. 600/38–41
See application file for complete search history.

(56) References Cited

U.S. PATENT DOCUMENTS

| 4,175,554 | A | * | 11/1979 | Gerow | 600/38 |
| 4,718,411 | A | * | 1/1988 | Stewart | 600/38 |
| 4,753,227 | A | | 6/1988 | Yanuck, Jr. | |
| 4,856,498 | A | | 8/1989 | Osbon | |
| 4,856,499 | A | * | 8/1989 | Kelly | 600/38 |
| 5,083,556 | A | | 1/1992 | Osbon et al. | |
| 5,095,895 | A | | 3/1992 | Walsh | |
| 5,125,890 | A | * | 6/1992 | Merrill et al. | 600/39 |
| D330,081 | S | | 10/1992 | Walsh | |
| 5,234,401 | A | | 8/1993 | Yamanaka | |
| 5,344,389 | A | | 9/1994 | Walsdorft et al. | |
| 5,536,233 | A | | 7/1996 | Khouri | |
| 5,951,460 | A | | 9/1999 | Vollrath | |
| 6,036,635 | A | | 3/2000 | Altshuler | |
| 6,248,059 | B1 | | 6/2001 | Gamper et al. | |
| 6,277,062 | B1 | | 8/2001 | Vollrath et al. | |
| 6,398,720 | B1 | | 6/2002 | Dabal | |
| 6,793,620 | B1 | * | 9/2004 | Droznin et al. | 600/39 |

OTHER PUBLICATIONS www.edenfantasys.com; pumps, toys; internet; as of Nov. 8, 2007.
www.pumptoys.com; mity-vac hand vacuum pumps; internet; as of Jul. 6, 2007.
www.monster-tube.com; monster tube; internet; as of Jul. 6, 2007.
www.zoinkerz.com; Master E Bio; internet; as of Jul. 6, 2007.

* cited by examiner

*Primary Examiner* — John Lacyk

(57) ABSTRACT

A male penile enhancer apparatus featuring an elongated tube. The elongated tube has a proximal end, a distal end, and an inner cavity; an opening disposed at the proximal end for insertion of a penis; a means for adjusting the diameter of the opening; and a means of withdrawing air from the inner cavity of the tube and creating a vacuum. The means for withdrawing air from the inner cavity of the tube and creating a vacuum may include an aperture disposed on the tube or an electric pump housed in a chamber disposed on the tube.

10 Claims, 8 Drawing Sheets

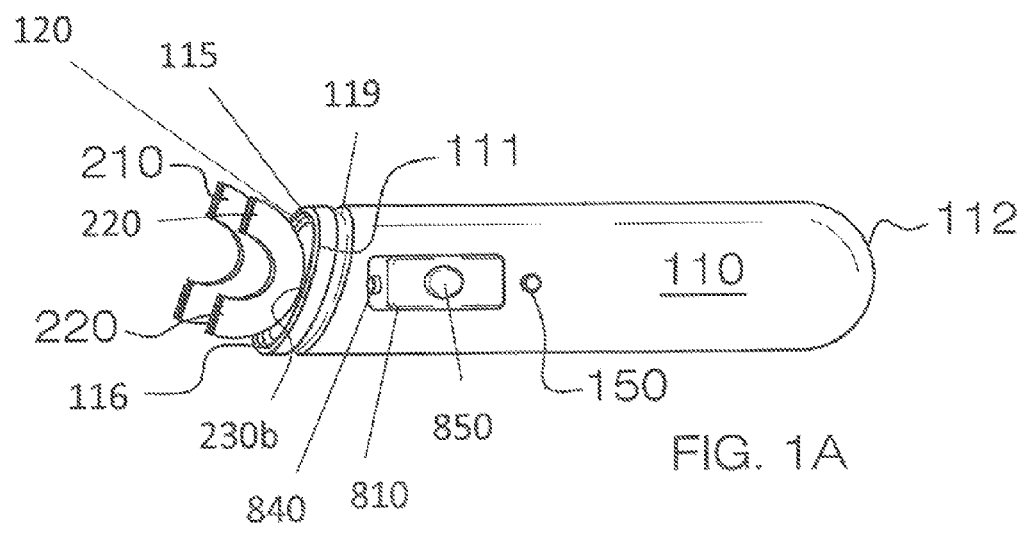
FIG. 1A
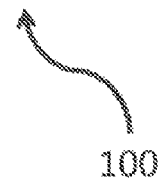
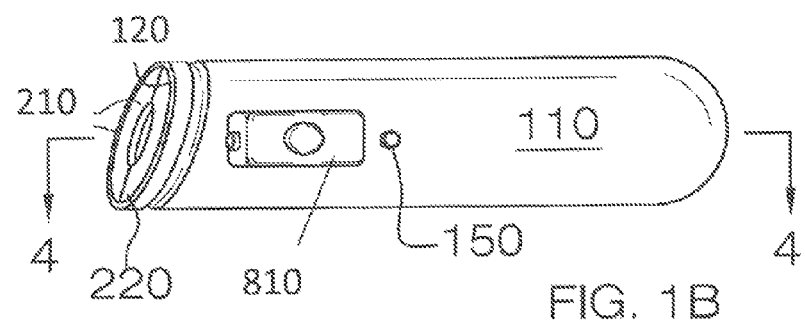
FIG. 1B

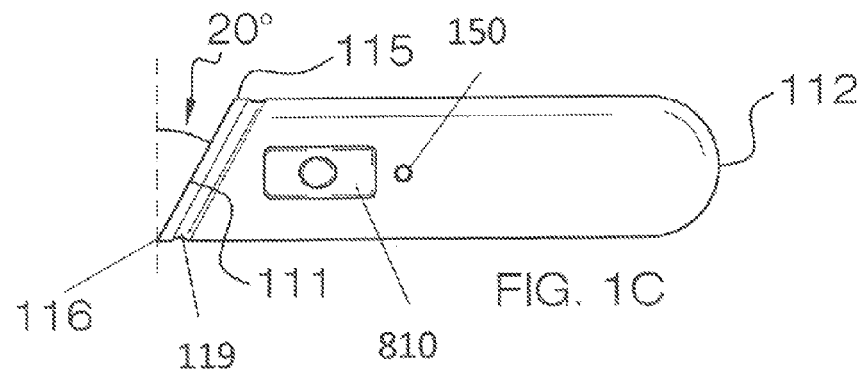
FIG. 1C
100
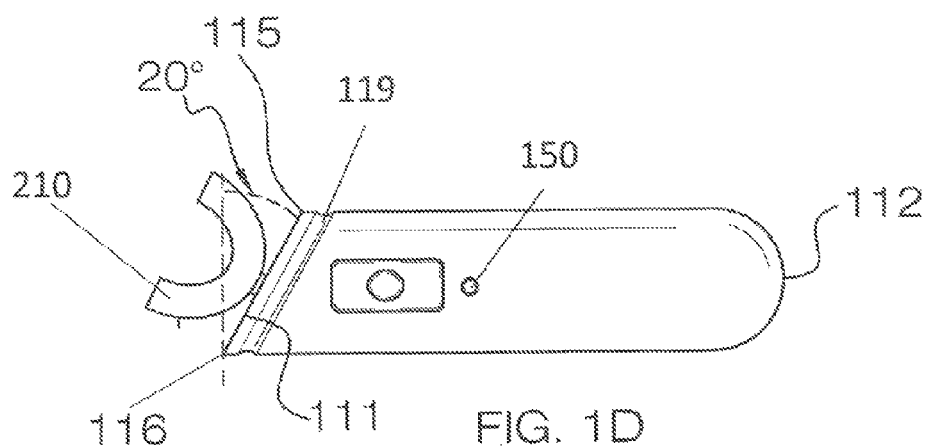
FIG. 1D

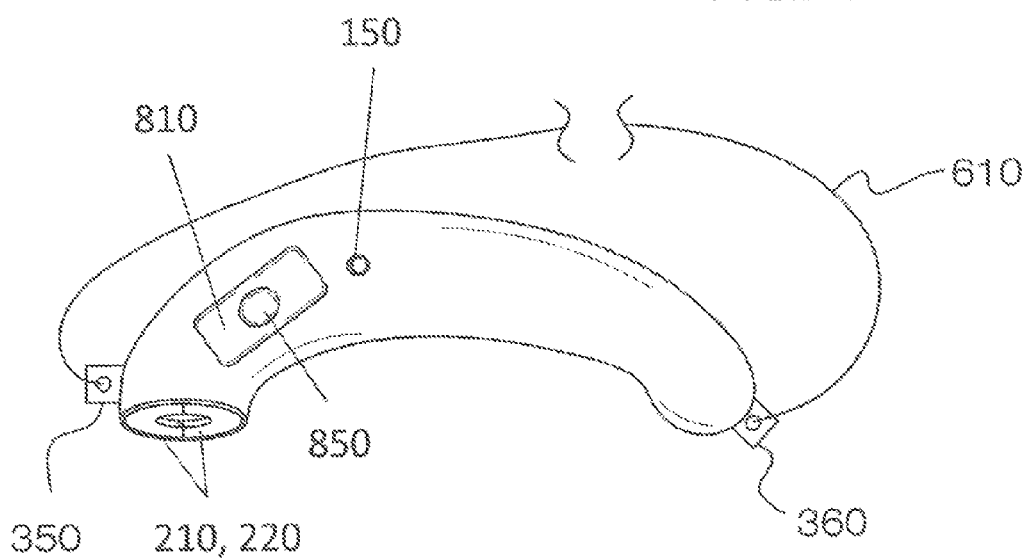

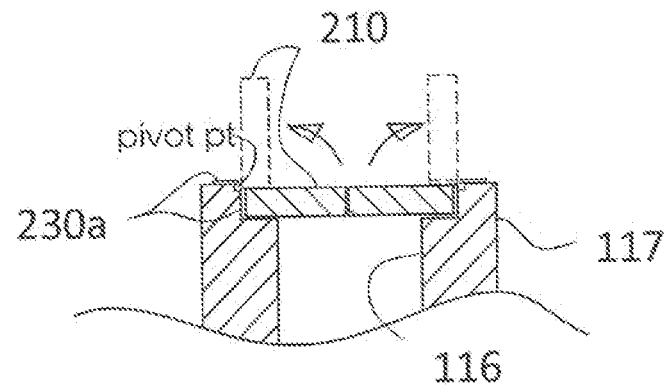
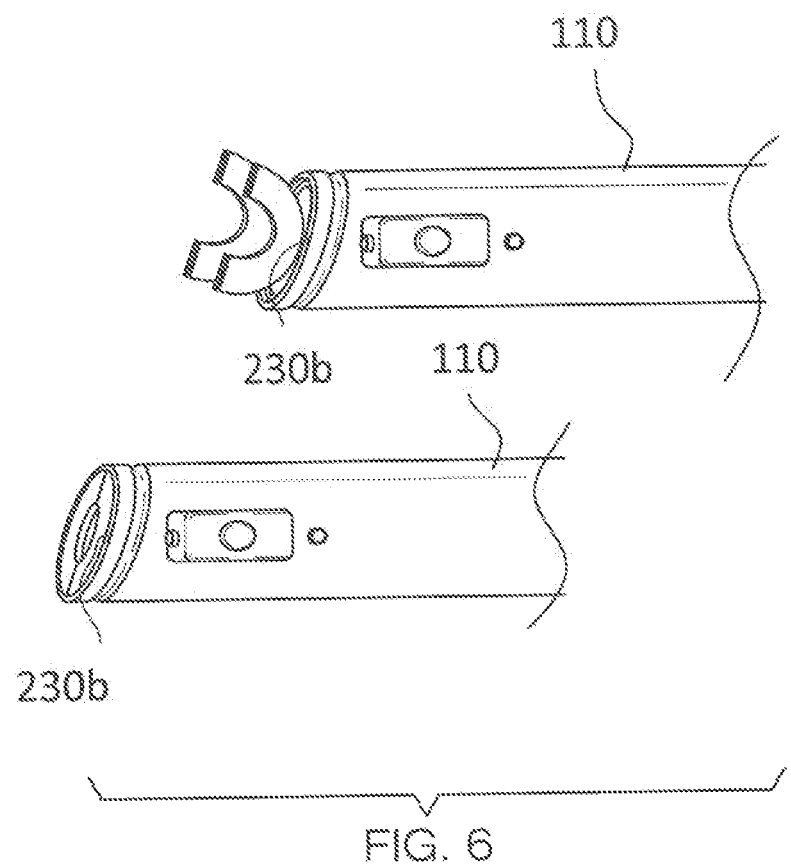
FIG. 6

PENILE ENHANCER APPARATUS

FIELD OF THE INVENTION

The present invention is directed to a device and methods for enhancement and enlargement of human organs, more particularly to a device for enhancing the size of the human penis organ.

BACKGROUND OF THE INVENTION

Penile enhancer devices are well known to one of ordinary skill in the art. The present invention features a novel penile enhancer apparatus.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1A is a first side view of the apparatus of the present invention.

FIG. 1B is a second side view of the apparatus of the present invention.

FIG. 1C is a third side view of the apparatus of the present invention.

FIG. 1D is a fourth side view of the apparatus of the present invention.

FIG. 1E is a fifth side view of the apparatus of the present invention.

FIG. 6 is a series of side views of the apparatus of the present invention

DESCRIPTION OF PREFERRED EMBODIMENTS

Figure 2:
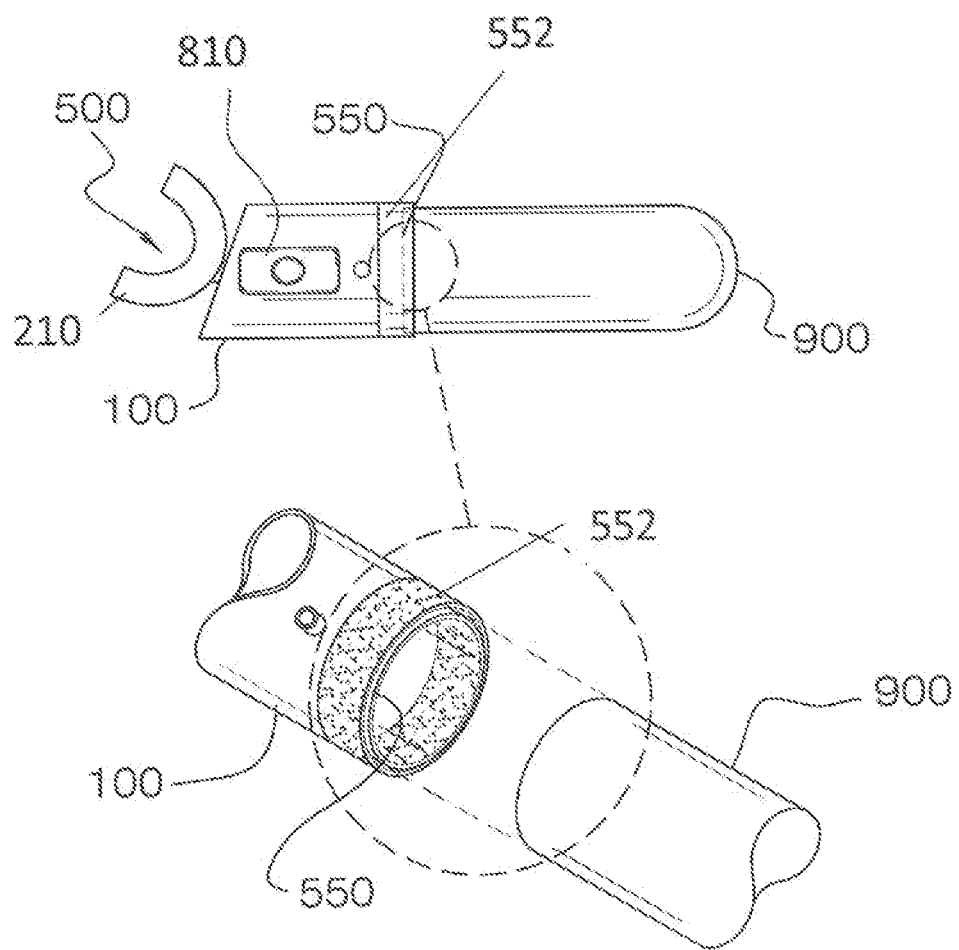
FIG. 2 is a detailed view of the apparatus of the present invention functioning as an adapter.

Referring now to FIGS. 1-6, the present invention features a penile enhancer apparatus 100 comprising an elongated tube 110 having a proximal end 111 and a distal end 112. In some embodiments, the tube 110 is a straight tube. In some embodiments, the tube 110 is a bent tube. In some embodiments, the tube 110 is a curved tube (e.g., see FIG. 1E). In some embodiments, the tube 110 has an inner wall 116 and an outer wall 117 (e.g., see FIG. 4).

A first opening 120 is disposed at the proximal end 111 for insertion of a penis. In some embodiments, a base groove 119 is disposed at the proximal end (e.g., for comfort). In some embodiments, the proximal end 111 is angled, for example the proximal end 111 is formed at an angle with respect to an upper lip 115 and lower lip 116 of the opening. Without wishing to limit the present invention to any theory or mechanism, it is believed that the angled proximal end 111 is advantageous because it allows for a more comfortable and better anatomic fit while the apparatus is in use.

The angle may be of various sizes (e.g., see FIG. 1C, 1D). For example, in some embodiments, the angle is about 20 degrees. In some embodiments, the angle is between about 5 to 10 degrees. In some embodiments, the angle is between about 10 to 15 degrees. In some embodiments, the angle is between about 15 to 20 degrees. In some embodiments, the angle is between about 20 to 25 degrees. In some embodiments, the angle is between about 25 to 30 degrees. In some embodiments, the angle is more than about 30 degrees.

As used herein, the term "about" refers to plus or minus 10% of the referenced number. For example, an embodiment wherein the angle is about 20 degrees includes an angle that is between 18 and 22 degrees.

The diameter of the first opening 120 can be adjusted, for example via an adjustment means. In some embodiments, the adjustment means comprises opposing doors, for example a first door 210 and a second door 220 that are arranged on opposing sides of the first opening 120 (e.g., upper lip 115 and lower lip 116, or first side and second side). The first door 210 is pivotally attached to the first opening 120 via first hinges 230a and the second door 220 is pivotally attached to the first opening 120 via second hinges 230b. As shown in FIG. 6, the first door 210 and second door 220 can move between a closed position wherein the doors cover a portion of the first opening 120 and an open position wherein the doors do not cover a portion of the first opening 120. When the doors 210, 220 are in the closed position, the doors 210, 220 may be secured together via a snap mechanism (e.g., interlocking joints 228, see FIG. 4).

The first door 210 and second door 220 may have a generally rounded U-shape. When both doors are in the closed position, second opening is formed wherein the second opening is a portion of the first opening 120. The diameter of the second opening is less than that of the first opening 120. The doors may be interchangeable to provide for various second openings with various reduced diameters.

Without wishing to limit the present invention to any theory or mechanism, it is believed that the ability to adjust the diameter of the opening of the proximal end (e.g., first opening 120, second opening) is advantageous because it may help reduce the area of the abdomen exposed to negative air pressure when the apparatus 100 is attached to a vacuum pump. Also, the adjustable diameter allows a user to increase the diameter as he achieves an erection.

The apparatus 100 of the present invention further comprises an aperture 150 disposed on the tube 110 for withdrawing air and creating a vacuum in the apparatus 100. A vacuum pump can be attached to the aperture 150. Vacuum pumps are well known to one of ordinary skill in the art. In some embodiments, the aperture 150 is a one-way valve 157 (see FIG. 4).

As shown in FIG. 1E, in some embodiments, the apparatus 100 further comprises a strap 610 attachable to the tube 110. The strap 610 may be used with the curved tube 110. The strap 610 may help to secure the apparatus 100 in place if a user is walking or moving. In some embodiments, the first end of the strap 610 attaches to a base attachment ring 350 at or near the proximal end 111 of the tube 110. In some embodiments, the second end of the strap 610 attaches to a top attachment ring 360 at or near the distal end 112 of the tube 110.

As shown in FIG. 2, in some embodiments, the apparatus 100 of the present invention can be used as an adaptor 500 for a second penile enhancer tube 900. For example, in some embodiments, the distal end 112 of the apparatus 100 comprises a connector means 550 to fluidly engage the second enhancer tube 900. The connector means 550 may be a telescopic joint. For example, the distal end 112 of the apparatus 100 may telescopically receive the outer end of the second penile enhancer tube 900. In some embodiments, a rubber coating 552 is disposed on the connector means 550 to help secure the apparatus 100 and second penile enhancer tube 900 together.

Figure 3:
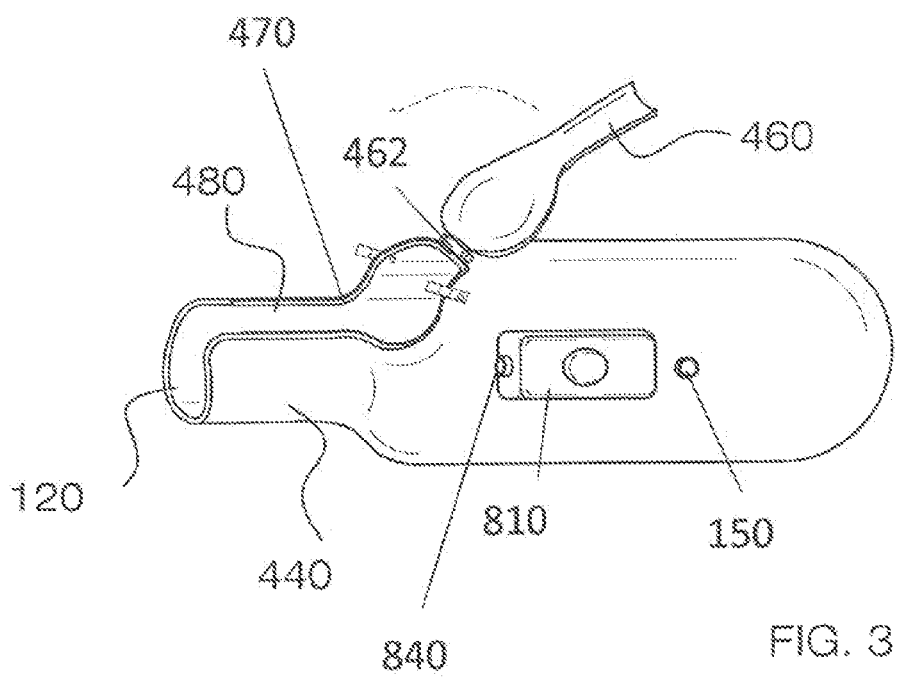
FIG. 3 is a side view of an alternative embodiment of the apparatus of the present invention.
Figure 4:
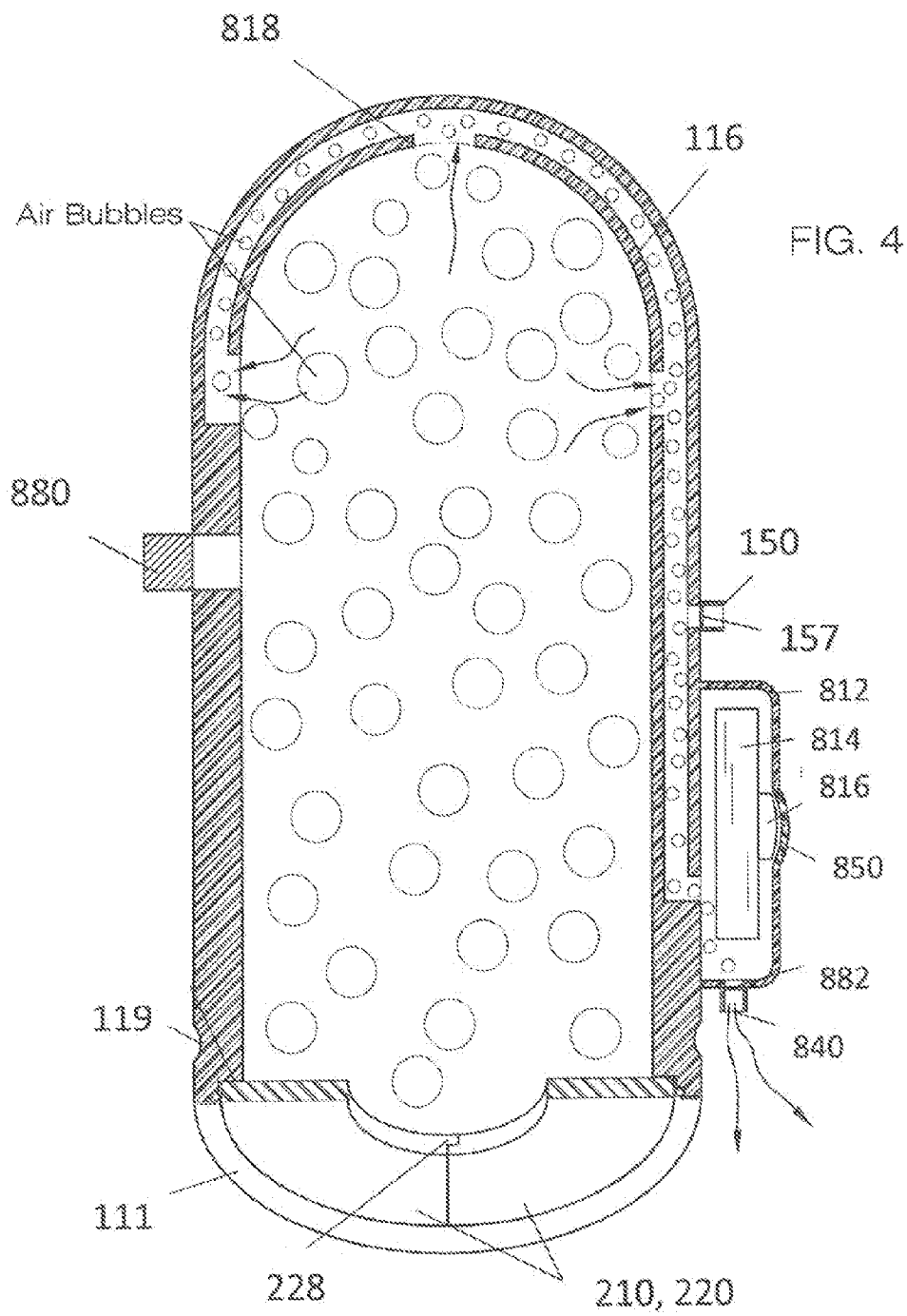
FIG. 4 is a top cross sectional view of the apparatus of the present invention.

As shown in FIG. 3, in some embodiments, the apparatus 100 further comprises a neck region 440 disposed at the proximal end 111 (e.g., an extension of the proximal end 111). The neck region 440 has a smaller diameter as compared to the remainder of the tube 110 (e.g., the region extending towards the distal end 112) (see FIG. 3).

In some embodiments, a cut 480 is disposed along the length of the elongated tube 110 or a portion thereof. As shown in FIG. 3, the cut 480 is disposed along a top edge of the neck region 440 (e.g. the proximal end 111 of the tube 110). The cut 480 separates a lid 460 from the rest of the tube 110. The lid 460 is pivotally attached to an edge of the cut 480 (e.g., a distal edge of the cut 480) via a lid hinge 462. The lid 460 can move between at least an open position (see FIG. 3, the lid 460 is pivoted away from the proximal end 111 of the tube 110) and a closed position. When the lid 460 is opened, a user can place his penis into the tube 110. When the lid 460 is closed, the lid 460 forms an opening at the proximal end 111 that can snugly fit around the penis that is inserted into the elongated tube 110. In some embodiments, a gasket 470 is disposed along all or a portion of the cut 480. This can help provide an air-tight seal when the lid 460 is moved to the closed position.

Figure 5:
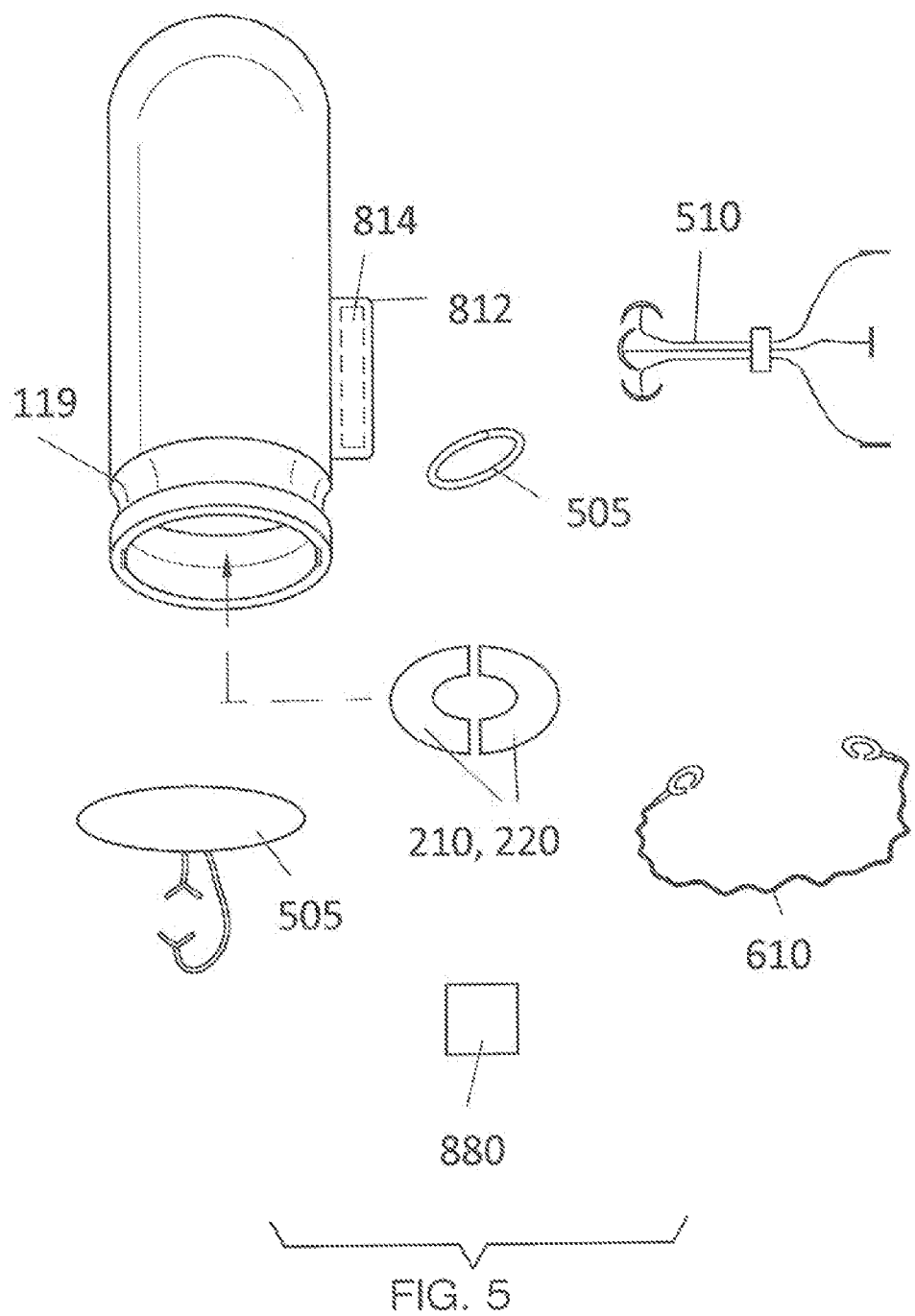
FIG. 5 is an exploded view of the components of the apparatus of the present invention.

As shown in FIG. 5, in some embodiments, the apparatus 100 is used in combination with a harness 505 for helping the apparatus 100 remain comfortably secured to the user. In some embodiments, the apparatus 100 is used in combination with a rubber band 508, wherein the rubber band 508 functions to constrict the penis while the apparatus 100 is being used (or after its use). In some embodiments, a rubber band extender 510 is used with the rubber band 508.

The apparatus 100 of the present invention further comprises an electric pump chamber 810 disposed on the tube 110. The electric pump chamber 810 comprises a chamber 812 for housing an electric pump 814. Electric pumps 814 are well known to one of ordinary skill in the art. The electric pump 814 comprises an on/off button 816, which is disposed on the outer surface (or accessible via the outer surface) of the chamber 812. In some embodiments, a rubber surface 850 covers the on/off button 816.

The chamber 812 is fluidly connected to the inner cavity of the tube 100 via an inner channel disposed in between the inner wall 116 and the outer wall 117 of the tube 110 and one or more inner wall apertures 818 disposed in the inner wall 116 of the tube 110. The electric pump 814 functions to draw air (e.g., air bubbles) from the inner cavity of the tube out of an, air exit port 840 disposed in the chamber 812 (via the inner wall apertures 118 and inner channel). The exit port 840 may comprise a one-way valve 882.

In some embodiments, the apparatus 100 further comprises a safety sensor valve 880 disposed in the tube 110. The safety sensor valve 880 functions to detect if the vacuum inside the inner cavity of the tube 110 is too strong, thereby letting a small amount of air into the inner cavity of the tube 110. Such safety valves are well known to one of ordinary skill in the art.

The apparatus 100 may be constructed in a variety of sizes. For example, in some embodiments, the tube 110 is between about 8 to 10 inches (e.g., 9.5 inches) in length as measured from the proximal end 111 to the distal end 112. In some embodiments, the tube 110 is between about 10 to 12 inches (e.g., 10.5 inches) in length as measured from the proximal end 111 to the distal end 112. In some embodiments, the tube 110 is less than about 8 inches or more than about 12 inches in length.

The present invention also features a method of enhancing the penis comprising attachment of the apparatus 100 of the present invention to the penis. The proximal end 111 comes in contact or is positioned near the user's abdomen. The apparatus 100 has the capacity to generate a vacuum via a vacuum pump connected to the aperture 150. The vacuum pump can be activated for a period of time.

The following the disclosures of the following U.S. Patents are incorporated in their entirety by reference herein: U.S. Pat. No. 6,398,720; U.S. Pat. No. 6,036,635; U.S. Pat. No. 4,753,227; U.S. Pat. No. 5,234,401; U.S. Pat. No. 4,856,498; U.S. Design Pat. No. D330,081.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A male penile enhancer apparatus, the apparatus comprising an elongated tube comprising:
   (a) a proximal end, a distal end, and an inner cavity;
   (b) an opening disposed at the proximal end for insertion of a penis;
   (c) a means for adjusting the diameter of the opening; and
   (d) a means of withdrawing air from the inner cavity of the tube and creatin a vacuum;

wherein the means for adjusting the diameter of the opening comprises a set of generally U-shaped doors that are arranged on opposing sides of a lip of the opening, wherein when the doors are in a closed position a second opening is formed from the door with a reduced diameter.

2. The apparatus of claim 1 wherein the set of doors are interchangeable to provide for various second opening with specific reduced diameter.

3. A male penile enhancer apparatus, the apparatus comprising an elongated tube comprising:
   (a) a proximal end and a distal end;
   (b) a neck region disposed at the proximal end, the neck region has a smaller diameter as compared to the distal end of the tube;
   (c) a cut disposed along all or a portion of a length of a top edge of the neck region;
   (d) a lid pivotally attached to an edge of the cut via a lid hinge, the lid can pivot between at least an open position and a closed position, when the lid is closed the lid forms an opening at the proximal end which can snugly fit around a penis that is inserted into the tube; and
   (e) a means of withdrawing air from the inner cavity of the tube and creating a vacuum.

4. The apparatus of claim 3 wherein the tube is a straight tube.

5. The apparatus of claim 3 wherein the tube is a bent tube or a curved tube.

6. The apparatus of claim 3 wherein the proximal end is formed at an angle with respect to an upper lip and lower lip of the opening.

7. The apparatus of claim 6, wherein the angle is about 20 degrees.

8. The apparatus of claim 3, wherein the means of withdrawing air from the inner cavity of the tube and creating a vacuum comprises an aperture disposed on the tube.

9. The apparatus of claim 3, wherein the means of withdrawing air from the inner cavity of the tube and creating a vacuum comprises an electric pump housed in a chamber disposed on the tube, the electric pump is fluidly connected to the inner cavity of the tube via an inner channel disposed in between an inner wall and an outer wall of the tube and one or more inner wall apertures disposed in the inner wall of the tube, wherein the electric pump draws air from the inner cavity of the tube and pumps the air out of an exit port disposed in the chamber.

10. A male penile enhancer apparatus, the apparatus comprising an elongated tube comprising:

(a) a proximal end, a distal end, and an inner cavity;
(b) an opening disposed at the proximal end for insertion of a penis;
(c) a means for adjusting the diameter of the opening; and
(d) a means of withdrawing air from the inner cavity of the tube and creatin a vacuum comprising an electric pump housed in a chamber disposed on the tube, the electric pump is fluidly connected to the inner cavity of the tube via an inner channel disposed in between an inner wall and an outer wall of the tube and one or more inner wall apertures disposed in the inner wall of the tube, wherein the electric pump draws air from the inner cavity of the tube and pumps the air out of an exit port disposed in the chamber;

wherein the means for adjusting the diameter of the opening comprises a set of generally U-shaped doors that are arranged on opposing sides of a lip of the opening, wherein when the doors are in a closed position a second opening is formed from the door with a reduced diameter.

\* \* \* \* \*